United States Patent [19]

Klauke et al.

[11] 3,931,312
[45] Jan. 6, 1976

[54] NOVEL N(-DIFLUOROMETHYLMERCAPTOPHENYL) UREA COMPOUNDS AND HERBICIDAL COMPOSITIONS

[75] Inventors: Erich Klauke, Odenthal; Engelbert Kühle, Bergisch-Gladbach; Ludwig Eue, Cologne, all of Germany

[73] Assignee: Bayer Aktiengesellschaft, Leverkusen, Germany

[22] Filed: May 1, 1973

[21] Appl. No.: 356,261

Related U.S. Application Data

[63] Continuation of Ser. No. 87,589, Nov. 6, 1970, abandoned.

[30] Foreign Application Priority Data

Jan. 24, 1970 Germany............................ 2003143

[52] U.S. Cl................................ 260/553 A; 71/98
[51] Int. Cl.[2]........................................ C07C 127/19
[58] Field of Search................................ 260/553 A

[56] References Cited
FOREIGN PATENTS OR APPLICATIONS 1,576,194   7/1969   France
1,532,014   7/1968   France

*Primary Examiner*—James O. Thomas, Jr.
*Assistant Examiner*—G. Breitenstein
*Attorney, Agent, or Firm*—Burgess, Dinklage & Sprung

[57] ABSTRACT

Novel N-(Difluoromethylmercaptophenyl) urea compounds of the formula

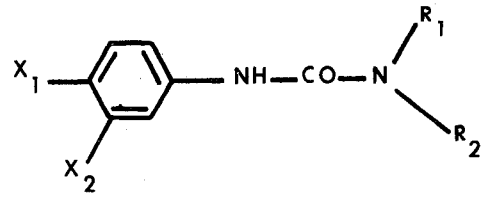

in which
  $X_1$ and $X_2$ individually are difluorochloromethylmercapto, chlorine or hydrogen, provided that at least one of $X_1$ or $X_2$ is difluorochloromethylmercapto;
  $R_1$ is hydrogen, alkyl of from 1 to 4 carbon atoms, or alkenyl of from 2 to 4 carbon atoms; and
  $R_2$ is alkyl of from 1 to 4 carbon atoms or alkenyl of from 2 to 4 carbon atoms;
are outstandingly effective as herbicides, particularly as selective herbicides.

8 Claims, No Drawings

NOVEL N(-DIFLUOROMETHYLMERCAPTOPHENYL) UREA COMPOUNDS AND HERBICIDAL COMPOSITIONS

This is a continuation of application Ser. No. 87,589, filed Nov. 6, 1970, now abandoned.

The present invention relates to certain new N-arylurea compounds, to herbicidal compositions containing them, and to their use as herbicides.

It is known that certain N-aryl-N-alkylurea compounds can be used as herbicides. Furthermore, it is known from Belgian Patent Specification 719,350 that a specific compound of this class, viz., N-(4-trifluoromethylmercaptophenyl)-N', N'-dimethylurea, can be used as a selective herbicide.

It has now been surprisingly found that the active compounds according to the present invention exhibit a higher degree of herbicidal activity, which at the same time is more sharply selective with respect to agricultural cultivated plants, that the known compound, trifluoromethylmercaptophenylurea.

The compounds of this invention are N-arylurea compounds of the general formula

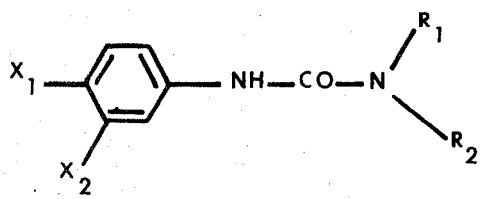

in which
X₁ and X₂ individually are difluorochloromethylmercapto, chlorine or hydrogen, provided that at least one of X₁ or
X₂ is difluorochloromethylmercapto;
R₁ is hydrogen, alkyl of from 1 to 4 carbon atoms, or alkenyl of from 2 to 4 carbon atoms; and
R₂ is alkyl of from 1 to 4 carbon atoms or alkenyl of from 2 to 4 carbon atoms.

The compounds responding to the above formula (I) have been found to exhibit strong herbicidal effectiveness, together with marked selectivity; i.e. non-damage to crops.

The present invention also provides a process for the production of the ureas of the formula (1) in which an isocyanate of the formula

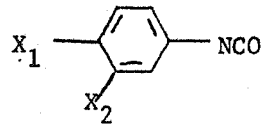

(2)

in which
X₁ and X₂ have the meanings stated above, is reacted with an amine of the formula

(3)

in which
R₁ and R₂ have the meanings stated above,
in the presence of a diluent (which term herein includes a solvent).

The reaction course when 4-difluorochloromethylmercaptophenylisocyanate and dimethylamine are used can be represented by the following equation:

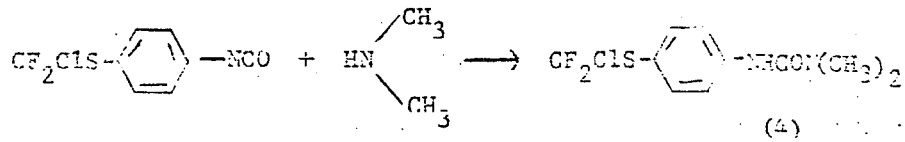

(4)

As further examples of isocyantes, there are mentioned: 3-chloro-4-difluorochloromethylmercapto-phenyl-isocyanate, 3-difluorochloromethylmercapto-phenyl-isocyanate and 3-difluorochloromethylmercapto-4-chloro-phenyl-isocyanate.

Suitable amines are, for example, methylamine, dimethylamine, methylethylamine, allylamine, butylamine, methylbutylamine and diallylamine.

As the diluent, water or any inert organic solvent is suitable. The preferred solvents include ethers, such as dioxane; hydrocarbons, such as benzene; chlorinated hydrocarbons, such as chlorobenzene; and ketones such as acetone.

The reaction temperatures can be varied within a fairly wide range; in general, the work is carried out at 10°–80°C, preferably at 20°–50°C.

When carrying out the process, approximately equimolar amounts of isocyanate and amine are preferably used, but an excess of amine is not detrimental. Working up takes place in the usual manner.

The active compounds according to the invention exhibit strong herbicidal properties. They can be used for the destruction of weeds. For purposes of this specification the term "weeds" is used in the widest sense, i.e. to embrace all plants which grow in cultivations or in other places where they are not desired. Whether the active compounds according to the invention act as total or selective herbicides depends essentially on the amount applied and on other conditions of application.

The substances according to the invention can be used e.g. in the case of the following plants: dicotyledons, such as mustard (Sinapis), cress (Lepidium), cleaver (Galium), common chick-weed (Stellaris), mayweed (Matricaria), smallflower Galinsoga (Galinsoga), fathen (Chenopodium), stinging nettle (Urtica), groundsel (Senecio), cotton (Gossypium), beets (Beta), carrots (Daucus), beans (Phaseolus), potatoes (Solanum), coffee (Coffea); monocotyledons, such as timothy (Phleum), bluegrass (Poa), fescue (Festuca), goosegrass (Eleusine), foxtail (Setaria), ryegrass (Lolium), cheat (Bromus), barnyard grass (Echinochloa), maize (Zea), rice (Oryza), oata (Avena), barley (Hordeum), wheat (Triticum), millet (Panicum), and sugar cane (Saccharum).

The active compounds according to the invention are particularly well suited for selective weed control in oats, wheat, maize, rice and cotton.

The active compounds according to the present invention can be converted into the usual formulations, such as solutions, emulsions, suspensions, powders, pastes and granulates. These may be produced in known manner, for example by mixing the active compounds with extenders, that is, liquid of solid diluents or carriers, optionally with the use of surface-active agents, that is emulsifying agents and/or dispersing agents. In the case of the use of water as an extender, organic solvents can, for example, also be used as auxiliary solvents. As liquid diluents or carriers, there are preferably used aromatic hydrocarbons, such as xylenes or benzene, chlorinated aromatic hydrocarbons, such as chlorobenzenes, paraffins, such as mineral oil fractions, alcohols, such as methanol or butanol or strongly polar solvents, such as dimethyl formamide or dimethyl sulphoxide, as well as water. As solid diluents or carriers, there are preferably used ground natural minerals, such as kaolins, clays, talc or chalk, or ground synthetic minerals, such as highly-dispersed silicic acid or silicates.

Preferred examples of emulsifying agents include non-ionic and anionic emulsifiers, such as polyoxyethylene-fatty acid esters, polyoxyethylene-fatty alcohol ethers, for example alkylarylpolyglycol ethers, alkyl sulphonates and aryl sulphnonates; and preferred examples of dispersing agents include lignin, sulphite waste liquors and methyl cellulose.

The active compounds according to the invention may be present in the formulations in admixture with other active compounds.

The formulations contain, in general, from 0.1 to 95, preferably from 0.5 to 90, percent by weight of active compound.

The active compounds may be applied as such or in the form of their formulations or of the application forms prepared therefrom, such as ready-to-use solutions, emulsions, suspensions, powders, pastes and granulates. Application may take place in any usual manner, for example by spraying, atomising, watering, dusting or scattering.

The active compounds can be applied according to the pre-emergence process and, with particularly good results, according to the post-emergence process.

The amount of active compound applied per unit area varies, according to the purpose of application and the nature of application. In general, from 0.5 to 20 kg of active compound per hectare, preferably 1 to 8 kg per hectare, are applied.

The active compounds according to the invention also possess insecticidal, acaricidal and fungicidal effectiveness, particularly against mould fungi; they also act against bacteria and yeasts.

The present invention in another aspects, also provides a herbicidal composition containing as active ingredient a urea of the present invention in admixture with a solid diluent or carrier or in admixture with a liquid diluent or carrier containing a surface-active agent. Furthermore, the invention provides a method of combating weeds which comprises applying to the weeds or a weed habitat a urea of the present invention alone or in the form of a composition containg as active ingredient a urea of the present invention in admixture with a solid or liquid diluent or carrier.

The effectiveness of the compounds of the invention is illustrated in and by the following Examples, wherein the following test compounds, illustrative of the invention, were used:

| Test Compound No. | Chemical Name | Structure |
|---|---|---|
| Compound 1 | N-(4-difluorochloromethyl-mercaptophenyl)-N',N'-dimethylurea | $F_2ClCS-\text{C}_6H_4-NH-C(=O)-N(CH_3)_2$ (para) |
| Compound 2 | N-(3-difluorochloromethyl-mercaptophenyl)-N',N'-dimethylurea | $F_2ClCS-\text{C}_6H_4-NH-C(=O)-N(CH_3)_2$ (meta) |
| Compound 3 | N-(3-chloro-4-difluoro-chloromethylmercaptophenyl)-N',N'-dimethylurea | $F_2ClCS-\text{C}_6H_3(Cl)-NH-C(=O)-N(CH_3)_2$ |

EXAMPLE A

Pre-emergence test

Solvent: 5 parts by weight acetone
Emulsifier: 1 part by weight alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0–5, which have the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

The active compounds, the amounts applied and the results obtained can be seen from the following Table:

Table A

| Active compound | Amount of active compound applied kg/hectare | Pre-emergence test Echino-chloa | Cheno-podium | Sina-pis | Stella-ria | Oats | Cotton | Wheat | Maize |
|---|---|---|---|---|---|---|---|---|---|
| $F_3CS-\text{C}_6H_3(Cl)-NH-C(=O)-N(CH_3)_2$ | 5 | 4 | 5 | 5 | 5 | 0 | 0 | 0 | 1–2 |
| | 2.5 | 3 | 3 | 3 | 5 | 0 | 0 | 0 | 1 |
| | 1.25 | 2 | 2–3 | 2 | 5 | 0 | 0 | 0 | 0 |
| (known) $F_3CS-\text{C}_6H_4-NH-C(=O)-N(CH_3)_2$ | 5 | 5 | 5 | 5 | 5 | 4 | 0 | 1 | 2 |
| | 2.5 | 5 | 5 | 4 | 5 | 3 | 0 | 0 | 1 |
| | 1.25 | 4 | 4 | 3 | 5 | 1 | 0 | 0 | 0 |
| (known) Compound 1 | 5 | 5 | 5 | 5 | 5 | 2 | 1 | 1 | 0 |
| | 2.5 | 4 | 5 | 4 | 5 | 1 | 0 | 0 | 0 |
| | 1.25 | 3 | 5 | 3 | 5 | 0 | 0 | 0 | 0 |
| Compound 2 | 5 | 5 | 5 | 5 | 5 | 2 | 1 | 1 | 0 |
| | 2.5 | 4–5 | 5 | 4 | 5 | 1 | 0 | 0 | 0 |
| | 1.25 | 4 | 4–5 | 3 | 5 | 0 | 0 | 0 | 0 |
| Compound 3 | 5 | 4–5 | 5 | 5 | 5 | 1 | 1 | 0 | 0 |
| | 2.5 | 3–4 | 5 | 5 | 5 | 0 | 0 | 0 | 0 |
| | 1.25 | 3 | 5 | 4 | 5 | 0 | 0 | 0 | 0 |

EXAMPLE B

Post-emergence test

Solvent: 5 parts by weight acetone
Emulsifier: 1 part by weight alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of about 5–15 cm. were sprayed with the preparation of active compound so that the amounts of active compound per unit area which was stated in the Table were applied. Depending on the concentration of the spray liquor, the amount of water applied lies between 1000 and 2000 l/ hectare. After 3 weeks, the degree of damage to the plants was determined and characterized by the values 0–5, which have the following meanings:

0 no effect
1 a few slightly burnt spots
2 marked damage to leaves
3 some leaves and parts of stalks partially dead
4. plant partially destroyed
5 plant completely dead.

The active compounds, the amounts applied and the results can be seen from the following Table:

Table B

| Active compound | Amount of active compound applied kg/hectare | Post-emergence test Echino-chloa | Cheno-podium | Sina-pis | Stella-ria | Urtica | Cotton | Wheat |
|---|---|---|---|---|---|---|---|---|
| $F_3CS-\text{C}_6H_4-NH-C(=O)-N(CH_3)_2$ | 2 | 5 | 5 | 5 | 5 | 5 | 2 | 0 |
| | 1 | 5 | 5 | 5 | 5 | 5 | 2 | 0 |
| (known) | 0.5 | 3–4 | 5 | 4–5 | 5 | 5 | 1 | 0 |
| $F_3CS-\text{C}_6H_3(Cl)-NH-C(=O)-N(CH_3)_2$ | 2 | 5 | 5 | 5 | 5 | 5 | 4–5 | 5 |
| | 1 | 5 | 5 | 5 | 5 | 5 | 3 | 4 |
| (known) | 0.5 | 4–5 | 5 | 5 | 5 | 5 | 2 | 3–4 |
| Compound 1 | 2 | 5 | 5 | 5 | 5 | 5 | 2 | 2 |
| | 1 | 5 | 5 | 5 | 5 | 5 | 1 | 1 |
| | 0.5 | 5 | 5 | 5 | 5 | 5 | 0 | 0 |
| Compound 2 | 2 | 5 | 5 | 5 | 5 | 5 | 2 | 2 |
| | 1 | 5 | 4–5 | 5 | 5 | 5 | 1 | 0 |
| | 0.5 | 5 | 4 | 5 | 4–5 | 5 | 0 | 0 |

Table B-continued

| Active compound | Amount of active compound applied kg/hectare | Post-emergence test Echinochloa | Chenopodium | Sinapis | Stellaria | Urtica | Cotton | Wheat |
|---|---|---|---|---|---|---|---|---|
| Compound 3 | 2 | 5 | 5 | 5 | 5 | 5 | 2 | 5 |
|  | 1 | 5 | 5 | 5 | 5 | 5 | 0 | 4–5 |
|  | 0.5 | 5 | 5 | 5 | 5 | 5 | 0 | 4 |

The process of the invention is illustrated in and by the following Examples.

EXAMPLE 1

Preparation of Compound 3

10 g 3-chloro-4-difluorochloromethylmercaptophenylisocyanate was added dropwise to 50 ml of a 20 percent — strength aqueous dimethylamine solution. The temperature was kept below 35°C by external cooling. The crystalline product was filtered off with section, and 11 g N-(3-chloro-4-difluoromethylmercaptophenyl)-N', N'-dimethylurea of m.p. 112°C were obtained.

The 3-chloro-4-difluorochloromethylmercaptophenyl-isocyanate was obtained by fluorination of 770 g 3-chloro-4-trichloromethylmercaptophenylisocyanate (b.p. 144°–147°C/0.8 mmHg, $n_D^{20}$ 1.6287) with 650 ml of anhydrous hydrofluoric acid at 0°–20°C. After distillation, there were obtained 502 g of the desired isocyanate of b.p. 139°C/14 mmHg, $n_D^{20}$ 1.5650.

In a manner analogous to that described above, there were obtained from this isocyanate the following ureas:

   m.p. 167°C

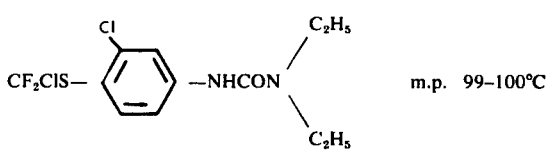   m.p. 99–100°C

   m.p. 107–108°C

EXAMPLE 2

Preparation of Compound 1

12 g 4-difluorochloromethylmercaptophenylisocyanate (b.p. 118°–120°C/16 mmHg, $n_D^{20}$ 1.5459) were dissolved in 50 ml acetone and added dropwise at room temperature to 50 ml of a 20 percent — strength aqueous dimethylamine solution, the temperature rose to about 30°C. The reaction product precipitated. Suction filtration was effected in the cold and 12 g N-(4-difluorochloromethylmercaptophenyl)-N', N'-dimethylurea of m.p. 142°–145°C were obtained.

EXAMPLE 3

Preparation of Compound 2

10.5 g 3-difluorochloromethylmercaptophenylisocyanate (b.p. 118°C/16 mm Hg, $n_D^{20}$ 1.5402) were added dropwise to 6 ml of a 50 percent — strength aqueous dimethylamine solution which was diluted with 50 ml acetone; stirring was effected for a time and the reaction product was precipitated with water. 12 g N-(3-difluorochloromethylmercaptophenyl)-N', N'-dimethylurea of m.p. 114°C were obtained.

It will be understood that the foregoing specification and examples are illustrative but not limitative of the present invention inasmuch as other embodiments within the spirit and scope of the invention will suggest themselves to those skilled in the art.

What is claimed is:

1. N-arylurea compound of the formula

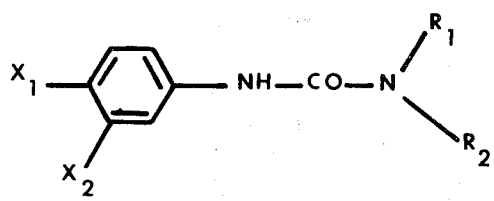

in which
X₁ and X₂ are difluorochloromethylmercapto, chlorine or hydrogen with the proviso that one and only one of $X_1$ and $X_2$ is difluorochloromethylmercapto;
$R_1$ is hydrogen, alkyl of from 1 to 4 carbon atoms; and
$R_2$ is alkyl of from 1 to 4 carbon atoms.

2. Compound as claimed in claim 1 wherein $X_1$ is difluorochloromethylmercapto.

3. Compound as claimed in claim 1 wherein $X_2$ is difluorochloromethylmercapto.

4. Compound as claimed in claim 1 wherein one of $X_1$ and $X_2$ is hydrogen.

5. Compound as claimed in claim 1 wherein one of $X_1$ and $X_2$ is chlorine.

6. Compound as claimed in claim 1 designated as N-(4-difluorochloromethylmercaptophenyl)-N', N'-dimethylurea.

7. Compound as claimed in claim 1 designated as N-(3-difluorochloromethylmercaptophenyl)-N', N'-dimethylurea.

8. Compound as claimed in claim 1 designated as N-(3-chloro-4-difluorochloromethylmercaptophenyl)-N', N'-dimethylurea.

* * * * *